United States Patent [19]

Braun et al.

[11] Patent Number: 4,754,069
[45] Date of Patent: Jun. 28, 1988

[54] 2-ALKYL SULFONYL-1,4-DIAMINOBENZENES, PROCESSES FOR THEIR PRODUCTION AND OXIDATION HAIR DYEING COMPOSITIONS CONTAINING THE SAME

[75] Inventors: Hans-Jürgen Braun, Marly; Eugen Konrad, Darmstadt; Herbert Mager, Fribourg, all of Fed. Rep. of Germany

[73] Assignee: Wella Aktiengesellschaft, Darmstadt, Fed. Rep. of Germany

[21] Appl. No.: 828,351
[22] PCT Filed: May 13, 1985
[86] PCT No.: PCT/EP85/00222
§ 371 Date: Dec. 12, 1985
§ 102(e) Date: Dec. 12, 1985
[87] PCT Pub. No.: WO86/00303
PCT Pub. Date: Jan. 16, 1986

[30] Foreign Application Priority Data

Jun. 29, 1984 [DE] Fed. Rep. of Germany ....... 3423933

[51] Int. Cl.$^4$ ...................... C07C 149/42; A61K 7/13
[52] U.S. Cl. ......................................... 564/440; 8/410; 8/416
[58] Field of Search ...................... 564/440; 8/410, 416

[56] References Cited

U.S. PATENT DOCUMENTS 3,118,943  1/1964  Buc et al. .............. 564/440
3,326,979  6/1967  Russell et al. ........ 564/440
3,687,567  9/1972  Shen et al. ............ 564/440

FOREIGN PATENT DOCUMENTS 0007537  6/1980  European Pat. Off. .

Primary Examiner—Glennon H. Hollrah
Assistant Examiner—John A. Sopp
Attorney, Agent, or Firm—Michael J. Striker

[57] ABSTRACT

Novel 2-alkyl sulfonyl ethyl-1,4-diaminobenzenes of formula 1

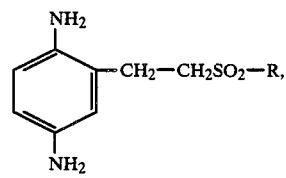

wherein R denotes $CH_3$ or $C_2H_5$ and the salts thereof, a process for making the compositions of formula I as well as compositions for the oxidative dyeing of human hair upon the basis of a developing substance-coupler substance-combination with a content of a composition of formula I as developing substance. The well water soluble developing substances of the formula I result in very natural appearing blond to brown color shades in combination with the coupler substances resorcinol, 4-chororesorcinol, 4,6-dichlororesorcinol, 4-hydroxy-1,2-methylenedioxybenzene and 4-amino-1,2-methylenedioxybenzene.

11 Claims, No Drawings

2-ALKYL SULFONYL-1,4-DIAMINOBENZENES, PROCESSES FOR THEIR PRODUCTION AND OXIDATION HAIR DYEING COMPOSITIONS CONTAINING THE SAME

The subject matter of the invention are compositions for the oxidative dyeing of hair on the basis of developing and coupler substances, whereby novel 2-alkyl sulfonyl-1,4-diaminobenzenes are used as the coupler substance.

Oxidation dyes have reched a substantial importance for hair dyeing. The dyeing is thereby generated by the reaction of specific developing substances with specific coupler substances in the presence of a suitable oxidation agent.

Preferably 2,5-diaminotoluene, 4-aminophenol and 1,4-diaminobenzene are used as developing substances, however 2,5-diaminoanisol, 2,5-diaminobenzyl alcohol and 2-($\beta$-hydroxyethyl)1,4-diaminobenzene have attained a certain importance. Tetraaminopyrimidine may also be used as a developing substance in certain cases.

For generating natural shades mainly resorcinol or 4-chlororesorcinol are used as coupler substances in conjunction with m-aminophenol. Instead of resorcinol one can also use 4-hydroxy-1,2-methylene dioxybenzene or 4-amino-1,2-methyllene dioxybenzene. Preferably 2,4-diamino phenol ether like 2,4-diaminoanisol, 2,4-diaminophenetol, 2,4-diamino phenoxy ethanol and 2-amino-4-(2'-hydroxyethylamino)-anisol are used for generating of blue constituents in black and ash shades. Furthermore, specific pyridine derivatives like, for example, 3,5-diamino-2,6-dimethoxy pyridine may be used as blue couplers. In addition to the mentioned compounds the coupler substances 4,6-dichlororesorcinol, 2-methyl resorcinol, 2,4-dihydroxy anisol, 5-amino-2-methylphenyl-1-naphtol, 4-aminohydroxy phenoxy ethanol and 4-hydroxyindol are of interest as shaders.

The described dye systems on the basis of the mentioned developing and coupler substances has been proven in practice, but it has some disadvantages which must be removed. For example, hair dyes are generated during the oxidative hair dyeing with the developing substances, 2,5-diaminotoluol or 1,4-diaminotoluene in combination with the coupler substances resorcinol or chlororesorcinol which do not appear natural, but show rusty appearing reflexes. As is known the desire for a natural hair coloring is particularly very well pronounced with women having heavily graying hair. This desire cannot be met sufficiently with the known oxidation hair dyeing compositions.

It had been repeatedly tried to remove the described disadvantages of the developing substances 2,5-diaminotoluene and 1,4-diaminobenzene, in that the hydrogen atoms on the amino groups of these molecules are substituted by specific residues, for example, carbamoyl methyl or hydroxyethyl. However, generally such substitution resulted in developing substances with degenerated dye characteristics. This degeneration shows in an insufficient dye balance and/or the complete missing of the formation of natural shades when using the customary developer in combination with resorcinol, 4-chlororesorcinol, 4-6-dichlororesorcinol, 4-hydroxy-1,2-methylene dioxybenzene and 4-amino-1,2-methylenedioxybenzene as coupler substances.

Surprisingly, it now had been found that, when replacing a hydrogen atom on the benzene core of the 1,4-diaminobenzene with an alkyl sulfonyl ethyl residue, the aforementioned disadvantages do not exist. These novel developing substances result in very natural appearing blond to brown color shades in combination with the coupler substances resorcinol, 4-chlororesorcinol, 4,6-dichlororesorcinol, 4-hydroxy-1,2-methylene dioxybenzene and 4-amino-1,2-methylene dioxybenzene.

Therefore, the subject matter of the present patent application are 2-alkyl sulfonyl ethyl-1,4-diamonobenzenes of formula I

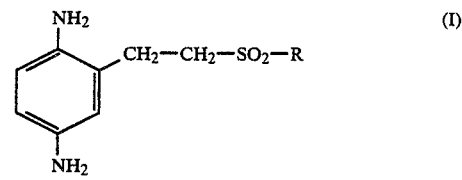

wherein R denotes $CH_3$ or $C_2H_5$, and the salts thereof as well as compositions for the oxidative dyeing of human hair on the basis of a developing substance-coupler substance combination, which contain as the developing substance a composition of formula I or the salts thereof.

The making of the novel 2-alkyl sulfonyl ethyl-1,4-diaminobenzenes is advantageously performed in eight synthesis steps in accordance with the following reaction pattern, whereby the basis of the reaction starts from the 2-nitrophenyl acetic acid (II) which is available in commercial amounts. This is reduced to the also known compound 2-nitrophenyl ethanol (III) with sodium borohydride in tetrahydrofurane. Therafter, the 2-nitrophenol ethanol is brominated with hydrogen bromide in concentrated sulfuric acid to the known compound 2-nitrophenylethylbromide (IV). The further synthesis is performed in that the 2-nitrophenylethylbromide is reacted with an alkylmercaptane to the new compound 2-alkyl-thioethyl-nitrobenzene (V), by oxidizing the alkylthioethyl-nitrobenzene with hydrogen peroxide into 2-alkyl sulfonyl ethyl nitrobenzene (VI), hydrating the 2-alkyl sulfonyl ethyl-nitrobenzene in the presence of acetic acid anhydride and palladium on charcoal to 2-alkyl sulfonyl ethyl-acetanilide (VII), nitrating the 2-alkyl sulfonyl ethyl acetanilide with $HNO_3/H_2SO_4$ to the 2-alkyl sulfonyl ethyl-4-nitroacetanilide (VIII) and reacting compound (VIII) with an ethanolic hydrochloric acid solution for deacetylizing and by finally converting the obtained 2-alkyl sulfonyl ethyl-4-nitroaniline (IX) in an ethanolic solution into the desired 2-alkyl sulfonyl ethyl-1,4-diaminobenzene (I) by hydrating in the presence of palladium on charcoal.

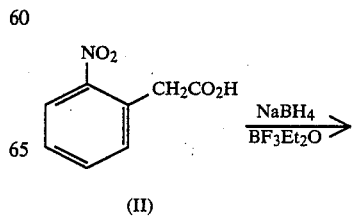

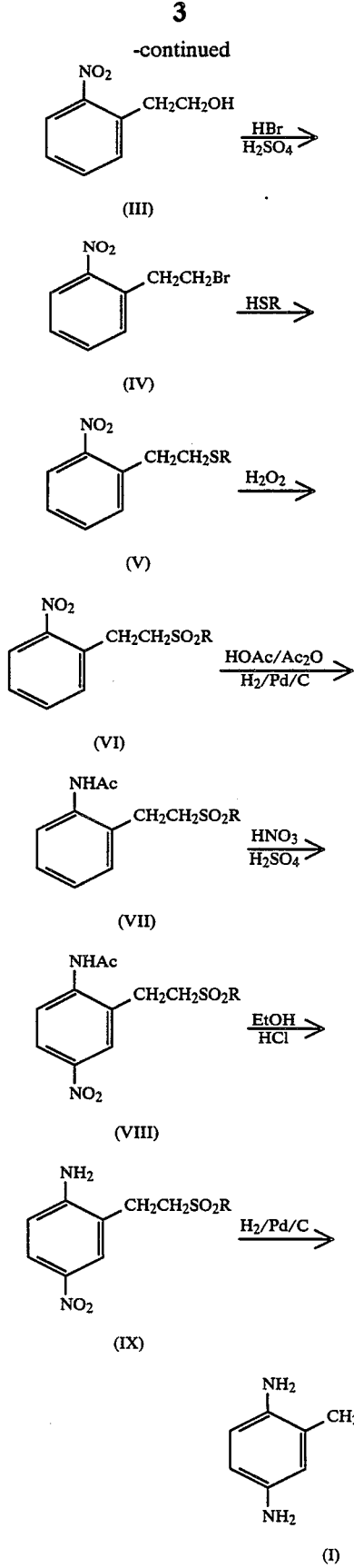

The novel developing substances of formula I are very well soluble in water and have an excellent storage capability, in particular as a component of the hair dyeing compositions described here.

If one uses the developing substance in accordance with the invention 2-methyl sulfonyl ethyl-1,4-diaminobenzene in combination with the known coupler substances resorcinol, 4-chlororesorcinol and 4,6-dichlororesorcinol, it can be noted that the intensity of the hair coloring obtained increases with each chlorine atom which is introduced into the resorcinol molecule in the stated sequence. Accordingly, the use of 2-methyl sulfonyl-1,4-diaminobenzene together with 4-chlororesorcinol and 4,6-dichlororesorcinol is preferred. Furthermore, very usable natural hair dyes can be generated with the coupler substances 4-hydroxy-1,2-methylene dioxy benzene and 4-amino-1,2-methylene dioxy benzene.

While the known developer substance 2,5-diaminotoluene in combination with 4,6-dichlororesorcinol results in intensive rusty colorations, which are not usable for the dye practice, the 4,6-dichlororesorcinol with the inventive developing substances of the formula I supplies substantially more natural and therefore more usable hair coloration. Moreover, the colorations are very uniform even with an increasing degree of damaging from the base of the hair to the tip of the hair.

A further important positive characteristic of the novel developing substance 2-methyl sulfonyl ethyl-1,4-diaminobenzene consists in that it is not mutagene, neither in the absence of the oxidation composition $H_2O_2$, nor after the reaction of $H_2O_2$ during the testing in a testing device in accordance with Ames.

The developing substances in accordance with the invention which are present in the hair dyeing composition, whereby the 2-methyl sulfonyl ethyl-1,4-diaminobenzene is preferred, should be contained therein in a concentration of about 0.01 to 4.0% by weight, preferably 0.1 to 2.5% by weight.

Although the advantageous characteristics of the described novel developing substances suggest to use them as sole developers, it is naturally also possible to use the novel developing substances of formula I together with known developing substances, for example, 4-aminophenol or 2,5-diaminotoluol.

Of the known coupler substances, above all, resorcinol, 4-chlororesorcinol, 4,6-dichlororesorcinol, 2-methylresorcinol, 2-amino-4-(2'-hydroxy ethyl amino)-anisol, 2,4-dihydroxy anisol, 2,4-dihydroxy phenoxy ethanol, 5-amino-2-methyl-phenol, 2,4-diaminophenoxyethanol, 4-amino-2-hydroxyphenoxyethanol, 1-naphthol, m-aminophenol, 3-amino-2-methylphenol, 3-amino-6-methylphenyl, 4-hydroxy-1,2-methylenedioxybenzene, 4-amino-1,2-methylenedioxybenzene, 4 (2'-hydroxyethylamino)-1,2-methylenedioxybenzene, 2,4-diaminoanisol and 2,4-diaminophenetol, 4-hydroxyindol and 3,5-diamino-2,6-dimethoxypyridine are considered as a component of the described hair dyeing compositions.

The mentioned coupler and developing substances may be contained in the hair dyeing compositions either individually or in a mixture with each other.

The total amount of the developer substance-coupler substance combination contained in the described hair dyeing compositions should be about 0.1 to 6.0% by weight, preferably 0.5 to 4.0% by weight.

The developing substances are generally used in about equimolar amounts with respect to the coupler components. However, it is not disadvantageous if the developing component is present in a certain excess or a lesser amount. In particular for obtaining mat shades it may be favorable to use the developing components to a lesser amount.

Furthermore, the hair dyeing compositions of this application may contain additional other dye components, for example, 6-amino-2-methyl-phenyl and 6-amino-3-methyl phenol, as well as further customary direct dyes, for example, triphenyl methane dyes like Diamond Fuchsine (C.I.42 510) and Leather Ruby HF (C.I. 42 520), aromatic nitro dyes like 2-nitro-1,4-diaminobenzene, 2-amino-4-nitrophenol, 2-amino-5-nitrophenol, 2-amino-4,6-dinitrophenol, 2-amino-5-(2'-hydroxyethylamino)-nitrobenzene and 2-methylamino-5-bis(2'-hydroxyethyl)-amino-nitrobenzene,azo dyes like Acid Brown 4 (C.I.14 805) and dispersion dyes, for example, 1,4-diaminoanthraquinone and 1,4,5,8-tetraaminoanthraquinone. These dye components may be contained in the hair dyeing compositions in an amount of about 0.1 to 4.0% by weight.

Naturally, the coupler and developing substances as well as the other dye components, as far as they are basic, may be used in form of the physiologically harmless acid addition salts like, for example, as hydrochloride or sulfate or, as far as they contain aromatic OH-groups, in form of the salts with bases, for example, as alkaliphenolates.

Moreover, further customary cosmetic additives may contained in the hair dyeing compositions, for example, antooxidants like ascorbic acid, thioglycolic acid or sodium sulfite, perfume oils, complex formers, wetting agents, emulsifiers, thickeners, caring agents and others.

The type of preparation may be, for example, a solution, in particular an aqueous or aqueous-alcoholic solution. Particularly preferred types of preparations are a creme, a gel or an emulsion.

Their composition represents a mixture of the dye components with the additives which are customary for such preparations.

Customary additives in solutions, cremes, emulsions or gels are, for example, solvents, like water, low aliphatic alcohols, for example, ethanol, propanol and isopropanol, or glycoles, like glycerine and 1,2-propylene glycol, furthermore wetting agents or emulsifiers from the classes of the anionic, cationic, amphoteric or nonionogenic surface active substances, like fatty alcohol sulfates, oxethylized fatty alcohol sulfates, alkyl sulfonates, alkylbenzene sulfonates, alkyltrimethyl ammonium salts, alkyl betaines, oxethylized nonylphenoles, fatty acid alkanolamides, oxethylized fatty acid esters, furthermore thickeners, like higher fatty acid alcohols, starch, cellulose derivatives, vaseline, paraffine oil and fatty acids as well as caring agents, like cationic resins, lanolin derivatives, cholesterin, pantothenic acid and betaine. The mentioned constituents are used in amounts which are customary for such purposes, for example, the wetting agents and emulsifiers in concentrations of about 0.5 to 30% by weight, the thickeners in an amount of about 0.1 to 25% by weight and the caring agents in a concentration of about 0.1 to 5.0% by weight.

Depending on the composition the hair dyeing composition in accordance with the invention they react weakly acid, neutral or alkaline. In particular they have a pH-value in the alkaline range between 8.0 and 11.5, whereby the adjustment is performed preferably with ammonia. However, organic amines may be used, for example, monoethanol amine and triethanol amine, or organic bases, like sodium hydroxyde and potassium hydroxide.

During use for the oxidative dyeing of hair the described hair dyeing composition on the basis of a developing substance-coupler substance combination and, if need be, other customary dye components is admixed with an oxidation composition shortly before use and carries an amount of the mixture which is sufficient for dyeing the hair, generally about 50 to 150 ml which is applied to the hair. Mainly hydrogen peroxide is considered as an oxidation composition for developing the hair dyeing, for example, in form of a 6% aqueous solution or its additive compositions of urea, melamine or sodium borate. The mixture is reacted on the hair at 15° to 50° for about 10 to 45 minutes, preferably for 30 minutes, subsequently the hair is rinsed with water and dried. If need be, a washing is performed with a shampoo after this rinsing and, if need be, an afterrinsing is performed with citric acid or wine vinegar, for example. Subsequently, the hair is dried.

The following examples will explain the subject matter of the invention in more detail.

MANUFACTURING EXAMPLE

Example 1

1. step

Manufacturing of 2-nitrophenyl ethyl alcohol (III)

91.0 g (0.5 Mol) 2-nitrophenyl acetic acid are dissolved in 500 ml tetrahydrofuran and reacted with 32,16 g (0.85 Mol) sodiumborhydride. After the hydrogen development fades 200 ml bortrifluordiethyletherate are added dro by drop for two hours. The mixture is stirred at room temperature for another 2 hours. Thereafter, 220 ml 2-normal hydrochloric acid solution are added drop by drop. The aqueous phase is extracted four times with 100 ml each diethyl ester. The ether phase is washed with 2-normal sodium carbonate solution and with water until it reacts neutral and dried over magnesium sulfate.

The oil (77 g) which remains during the removal of the ether is distilled in a vacuum. The fraction which boils at 115°–118° C./5 Pa (pascal) weighs 66 g. This corresponds to a yield of 78% of the theory. The literature[2] states a boiling point of 165°–167° C./6 Torr (=800 Pa) for composition III.
(2) Beilstein E II 6 (1944) 452

2. step

Manufacturing of 2-nitrophenylethylbromide (IV)

65 g (0.39 Mol) 2-nitrophenylethanol (III) are heated with 200 ml hydrobromic acid (48%) and 45 ml concentrated sulfuric acid for 18 hours to 110°. The mixture is extracted with methylene chloride; the organic extract is washed with 2-normal sodium carbonate solution and water until it reacts neutral and is dried over magesium sulfate. The oil (88 g) which remains after the removal of the methylene chloride is dissolved with 50 ml ethanol and cooled to 0° C. The desired product crystallizes after frictional engagement with a glas rod.

Yield: 71 g (80% of the theory)

Melting point: 35° to 36° C. (literature[3]: 36°–38° C.)
(3) E. L. Foreman and S.. M. McElvain J. Am. Chem. Soc. (1940) 1435–1438)

3. step

Manufacturing of 2-methylthioethyl-ntrobenzene 16.0 g (0.4 Mol) sodium hydroxide are dissolved in 120 ml water and 230 ml ethanol. 37 g (0.78 Mol) methyl mercaptane are fed into this solution. The mixture is heated to 90° C. and dissolved with 71 g (0.31 Mol) 2-nitrophenylethylbromide (IV) in 450 ml ethanol and reacted drop by drop during two hours.

After the solution had been boiled subsequently for one hour under a return flow, the ethanol is distilled off. The residue is reacted with water and extracted with methylene chloride. The oil (56 g) obtained from the methylene chloride phase can be distilled in the vacuum. It has a boiling point of 105°–106° C. at 3 Pa.

4. step

Manufacturing of 2-methyl sulfonyl ethyl-nitrobenzene 29.0 (0.15 Mol) 2-methylthioethyl-nitrobenzene are reacted drop by drop in 150 ml glacial acetic acid with 70 ml hydrogen peroxide (30% aqueous solution). The temperature of the mixture is maintained at 40° C. by cooling. Thereafter, the mixture is heated for one hour to 100° C. 300 ml water are added to the cooled solution, whereby the desired product precipitates crystalline. It is vacuumed off and recrystallized from ethanol.

Yield: 29 g (85% of the theory).
Melting point: 100°–101° C.

| CHN-analysis $C_9H_{11}NO_4S$ | | | |
|---|---|---|---|
| | % C | % H | % N |
| calculated: | 47.15 | 4.84 | 6.11 |
| found: | 47.14 | 4.83 | 6.10 |

5. step

Manufacturing of 2-methyl sulfonyl ethyl-acetanilide 8.0 g (35 mMol) 2-methyl sulfonyl ethyl-nitrobenzene are hydrated in a mixture of 160 ml glacial acetic acid and 160 ml acetic acid anhydride by adding 0.4 g palladium on charcoal (10% Pd). The catalyst is filtered off after three hours and the excess solvents are completely distilled off under a reduced pressure.

Yield (crude): 10 g.

A sample was recrystallized from ethanol for analysis.

Melting point: 142°–143° C.

| CHN-analysis: $C_{11}H_{15}NO_3S$ | | | |
|---|---|---|---|
| | % C | % H | % N |
| calculated: | 54.75 | 6.27 | 5.80 |
| found: | 54.72 | 6.28 | 5.74 |

6. and 7. step

Manufacturing of 2-methyl sulfonyl ethyl-4-nitroaniline

The crude product from step 5 is dissolved in 100 ml concentrated sulfuric acid, cooled to 0° C. and nitrated at 0° C. with 3.2 ml nitric acid (density: 1.52 kg/m³). The mixture is heated to room temperature during one hour and then poured onto ice. The separated product is vacuumed off, washed with water and dried.

The product is heated to a 100° C. with 150 ml ethanol and 50 ml hydrochloric acid (density 1.16 kg/m³) for half an hour. Thereafter, 100 ml water are added. The product which crystallized into yellow needles is vacuumed off and is recrystallized from 1,3 l ethanol.

Yield: 4.0 g (47% of the theory with respect to the charged 2-methylthioethyl-4-nitrobenzene).

Melting point: 197°–198° C.

| CHN-analysis: $C_9H_{12}N_2O_4S$ | | | |
|---|---|---|---|
| | % C | % H | % N |
| calculated: | 44.25 | 4.95 | 11.47 |
| found: | 44.26 | 4.95 | 11.53 |

8. step

Manufacturing of 2-methyl sulfonyl ethyl-1,4-diaminobenzenesulfate 2.0 g 2-methyl sulfonyl ethyl-4-nitroaniline are hydrated in 750 ml ethanol with 0.35 palladium on charcoal (10% Pd). A filtering off from the catalyst is performed after four hours. The filtrate is reacted with 20 ml 2-normal sulfuric acid. The precipitated product is vacuumed off, washed with ethanol and dried.

Yield: 2.5 g (100% of the theory) of a white powder is obtained.

| CHN-analysis: $C_9H_{14}O_2S.H_2SO_4$ | | | |
|---|---|---|---|
| | % C | % H | % N |
| calculated: | 34.61 | 5.16 | 8.97 |
| found: | 34.06 | 5.21 | 8.66 |

Titration: weight sample 31.0 mg; discharge of 0.01 normal; soda lye: 19.9 ml(calculated); 20.3 ml(found).

The free base can be recovered from a hydrogenation charge by reducing the ethanolic solution until the start of the crystallisation.

Melting point: the color less platelets of the reaction product melt at 147° to 149° C.

| CHN-analysis: $C_9H_{14}N_2O_2S$ | | | |
|---|---|---|---|
| | % C | % H | % N |
| calculated: | 50.45 | 6.58 | 13.07 |
| found: | 50.48 | 6.61 | 13.00 |

The 1,4-position of the amino groups in the synthesized compound results from the fact that it shows the characteristic color reaction for p-diamines during reaction with the customary couplers.

EXAMPLES FOR HAIR DYEING COMPOSITIONS

Example 2

Hair dyeing composition in form of a gel

| | |
|---|---|
| 0.5 g | 2-methyl sulfonyl ethyl-1,4-dichlororesorcinol-sulfate |
| 0.5 g | 4.6-dichlorresorcine |
| 0.3 g | ascorbic acid |
| 1.0 g | hydroxyethyl cellulose, highly viscous |
| 5.0 g | sodium lauryl alcohol diglycol ether sulfate (28% aqueous solution) |
| 10.0 g | ammonia, 25% |
| 87.7 g | water |
| 100.0 g | |

Shortly before use one mixes 50 g of this hair dyeing composition with 50 ml hydrogen peroxide solution (6%) and the mixture reacts for 30 minutes at 40° C. on blonded human hair. Therafter a rinsing is performed with water and dried. The hair has assumed a natural dark blond coloration.

Example 3

Hair dyeing composition in form of a gel

| | |
|---|---|
| 1.0 g | 2-methylsulfonyl ethyl-1,4-diaminobenzene-sulfate |
| 0.9 g | 4-amino-1,2-methylenedioxybenzene |
| 0.1 g | m-aminophenol |
| 0.3 g | ascorbic acid |
| 15.0 g | oleic acid |
| 7.0 g | isopropanol |
| 10.0 g | ammonia, 25% |
| 65.7 g | water |
| 100.0 g | |

Shortly before use one mixes 50 g of this hair dyeing composition with 50 ml hydrogen peroxide solution (6%) and the mixture is subsequently applied on gray human hair which is chemically not damaged. After a reaction time of 30 minutes at 40° C. it is rinsed with water and dried. The hair is dyed medium brown.

Example 4

Hair dyeing composition in form of a creme

| | |
|---|---|
| 3.0 g | methyl sulfonyl ethyl-1,4-diaminobenzene-sulfate |
| 1.2 g | 4-chlororesorcinol |
| 0.6 g | 2-amino-4-(2'hydroxyethylamino)-anisol-sulfate |
| 0.3 g | m-aminophenol |
| 0.3 g | sodium sulfite, free of water |
| 15,0 g | cetyl alcohol |
| 3.5 g | sodium lauryl alcohol diglycol ether sulfate (28% aqueous solution) |
| 8.0 g | ammonia, 25% |
| 68.1 g | water |
| 100.0 | |

Shortly before use one mixes 50 g of this hair dyeing composition with 50 ml hydrogen peroxide solution (6%) and the mixture is subsequently applied on blond human hair. After a reaction time of 30 minutes at 40° C. it is rinsed with water and dried. The hair is dyed in an intensive, natural black.

All percentage number stated in the application represent percentage by weight.

We claim:

1. 2-alkyl sulfonyl ethyl-1,4-diaminobenzene of formula I

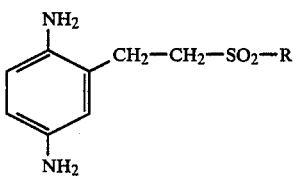

wherein R denotes $CH_3$ or $C_2H_5$ and the salts thereof.

2. 2-methyl sulfonyl ethyl-1,4-diaminobenzene and the salts thereof.

3. Composition for the oxidative dyeing of human hair upon the basis of one developing substance-coupler substance-combination, characterized in that it contains as the developing substance a 2-alkyl sulfonyl ethyl-1,4-diaminobenzene of formula I

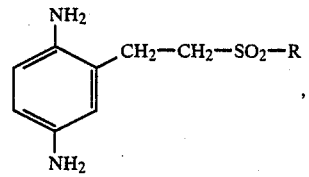

wherein R denotes $CH_3$ or $C_2H_5$, or contains the salts thereof.

4. Composition in accordance with claim 3, characterized in that it contains 2-methyl sulfonyl ethyl-1,4-diaminobenzene or the salts thereof as the developing substance.

5. Composition in accordance with claim 3, characterized in that it contains at least one of the coupler substances resorcinol, 2-methylresorcinol, 4-chlororesorcinol, 4,6-dichlororesorcinol, 4-hydroxy-1, 2-methylenedioxybenzene, 4-amino-1, 2-methylenedioxybenzene, 4-(2'-hydroxyethylamino)-1, 2-methylenedioxybenzene, 2,4-dihydroxyanisol, 2,4-dihydroxyphenoxyethanol, 4-amino-2-hydroxyphenoxyethanol, m-aminophenol, 5-amino-2-methyl-phenol, 1-naphthol, 4-hydroxyindol, 2,4-diaminoanisol, 2,4-diaminophenetol, 2-amino-4-(2'-hydroxyethylamino)-anisol, 2,4-diaminophenoxyethanol and 3,5-diamino-2,6-dimethoxypyridine.

6. Composition in accordance with claim 3, characterized that it contains a dye component which is selected from 6-amino-2-methyl-phenol, 6-amino-3-methylphenol, Diamond Fuchsine, (C.I.42 510), Leather Ruby HF (C.I.42 520), 2-nitro-1,4-diaminobenzene, 2-amino-4-nitrophenol, 2-amino-4,6-dinitrophenol, 2-amino-5-nitrophenol, 2-amino-5-(2'-hydroxyethylamino)-nitrobenzene, 2-methylamino-5-bis-(2'-hydroxyethyl)-aminonitrobenzene, Acid Brown 4 (C.I. 14 805), 1,4-diaminoanthraquinone and 1,4,5,8-tetraaminoanthraquinone.

7. Composition in accordance with claim 4, characterized in that it contains at least one of the coupler substances resorcinol, 2-methylresorcinol, 4-chlororesorcinol, 4,6-dichlororesorcinol, 4-hydroxy-1, 2-methylenedioxybenzene, 4-amino-1, 2-methylenedioxybenzene, 2,4-dihydroxyanisol, 2,4-dihydroxyphenoxyethanol, 4-amino-2-hydroxyphenoxyethanol, m-aminophenol, 5-amino-2-methyl-phenol-1-naphthol, 4-hydroxyindol, 2,4-diaminoanisol, 2,4-diaminophenetol, 2-amino-4-(2'-hydroxyethylamino)-anisol, 2,4-diaminophenoxyethanol and 3,5-diamino-2,6-dimethoxypyridine.

8. Composition in accordance with claim 3, characterized in that it contains the developing substance of formula I in an amount of 0.01 to 4.0% by weight.

9. Composition in accordance with claim 3, characterized in that the total amount of the coupler substance-developing substance-combination is 0.1 to 6.0% by weight.

10. Composition in accordance with claim 3, characterized in that it contains ascorbic acid, sodium sulfite or thioglycolic acid.

11. Composition in accordance with claim 3, characterized in that it contains 2-methyl sulfonyl ethyl-1,4-diaminobenzene or the salts thereof as the developing substance.

* * * * *